United States Patent
Irie et al.

(10) Patent No.: US 12,307,730 B2
(45) Date of Patent: May 20, 2025

(54) GATE APPARATUS, CONTROL METHOD OF GATE APPARATUS, AND STORAGE MEDIUM

(71) Applicant: NEC Corporation, Tokyo (JP)

(72) Inventors: Fumi Irie, Tokyo (JP); Yoshitaka Yoshimura, Tokyo (JP)

(73) Assignee: NEC CORPORATION, Tokyo (JP)

( * ) Notice: Subject to any disclaimer, the term of this patent is extended or adjusted under 35 U.S.C. 154(b) by 368 days.

(21) Appl. No.: 17/796,338

(22) PCT Filed: Feb. 18, 2020

(86) PCT No.: PCT/JP2020/006194
§ 371 (c)(1),
(2) Date: Jul. 29, 2022

(87) PCT Pub. No.: WO2021/166061
PCT Pub. Date: Aug. 26, 2021

(65) Prior Publication Data
US 2023/0067694 A1 Mar. 2, 2023

(51) Int. Cl.
*G06V 10/141* (2022.01)
*G03B 15/07* (2021.01)
(Continued)

(52) U.S. Cl.
CPC ........... *G06V 10/141* (2022.01); *G03B 15/07* (2013.01); *G06F 21/32* (2013.01); *G06T 7/70* (2017.01);
(Continued)

(58) Field of Classification Search
CPC ........ G07C 9/37; G07C 9/00; G07C 9/00563; G07C 9/25; G07C 9/26; G07C 9/253;
(Continued)

(56) References Cited

U.S. PATENT DOCUMENTS

| | | | | |
|---|---|---|---|---|
| 2003/0039380 A1* | 2/2003 | Sukegawa | ............... | G06F 18/28 382/118 |
| 2008/0302870 A1* | 12/2008 | Berini | ..................... | G07C 9/257 235/380 |

(Continued)

FOREIGN PATENT DOCUMENTS

| | | | |
|---|---|---|---|
| CN | 110059463 A | * | 7/2019 |
| JP | 2003-015211 A | | 1/2003 |

(Continued)

OTHER PUBLICATIONS

Search machine translation to Lu et al., Multiple Identity Verification and Identification System, translation Jan. 23, 2025, 10 pages. (Year: 2025).*

(Continued)

*Primary Examiner* — Henok Shiferaw
*Assistant Examiner* — Dennis Rosario

(57) ABSTRACT

A gate apparatus includes an upper light that emits light from above a user, a lower light that emits light from below the user, a light control unit, and an acquisition unit. The acquisition unit acquires biological information about the user. The light control unit changes the luminance of the light emitted from the upper light and the luminance of the light emitted from the lower light when the biological information about the user is acquired.

8 Claims, 13 Drawing Sheets

(51) Int. Cl.
| | |
|---|---|
| *G06F 21/32* | (2013.01) |
| *G06T 7/70* | (2017.01) |
| *G06V 40/00* | (2022.01) |
| *G06V 40/16* | (2022.01) |
| *G07C 9/10* | (2020.01) |
| *G07C 9/25* | (2020.01) |
| *G07C 9/37* | (2020.01) |

(52) U.S. Cl.
CPC ............. *G06V 40/00* (2022.01); *G06V 40/16* (2022.01); *G06V 40/166* (2022.01); *G06V 40/168* (2022.01); *G06V 40/172* (2022.01); *G07C 9/10* (2020.01); *G07C 9/25* (2020.01); *G07C 9/37* (2020.01); *G06T 2207/10152* (2013.01); *G06T 2207/30201* (2013.01)

(58) Field of Classification Search
CPC ..................... G07C 9/257; G07C 2009/00785; G07C 9/10; G06F 21/32; G06V 40/173; G06V 40/70; G06V 40/1365; G06V 40/12; G06V 40/14; G06V 40/45; G06V 40/18; G06V 40/11; G06V 40/117; G06V 40/113; G06V 40/107; G06V 40/1376; G06V 40/1371; G06V 40/40; G06V 40/60; G06V 40/63; G06V 40/67; G06V 40/1324; G06V 40/1347; G06V 10/145; G06V 10/14; G06V 10/141; G06V 10/143; G06V 10/147; G06V 40/171; G06V 40/168; G06V 40/16; G06V 40/174; G06V 40/19; G06V 40/00; G06V 40/10; G06V 40/103; G06V 40/13; G06V 40/1306; G06V 40/1312; G06V 40/1318; G06V 40/1329; G06V 40/1335; G06V 40/1341; G06V 40/1353; G06V 40/1359; G06V 40/1382; G06V 40/1388; G06V 40/1394; G06V 40/145; G06V 40/15; G06V 40/155; G06V 40/161; G06V 40/162; G06V 40/164; G06V 40/165; G06V 40/166; G06V 40/167; G06V 40/169; G06V 40/175; G06V 40/172; G06V 40/178; G06V 40/176; G06V 40/179; G06V 40/193; G06V 40/20; G06V 40/23; G06V 40/25; G06V 40/28; G06V 40/30; G06V 40/33; G06V 40/37; G06V 40/376; G06V 40/382; G06V 40/394; G06V 40/388; G06V 40/50; G06V 40/53; G06V 40/55; G06V 40/58; G06V 40/197; G06V 2201/03; G03B 15/02; G03B 15/07; G03B 15/03; G03B 15/035; G03B 15/04; G03B 15/0405; G03B 15/041; G03B 15/0415; G03B 15/0421; G03B 15/0426; G03B 15/0431; G03B 15/0436; G03B 15/0442; G03B 15/0447; G03B 15/0452; G03B 15/0457; G03B 15/0463; G03B 15/0468; G03B 15/0473; G03B 15/0484; G03B 15/0478; G03B 15/0489; G03B 15/0494; G03B 15/06; G03B 15/05; G06T 2207/30201; G06T 2207/30196; G06T 2207/30041; G06T 2207/30004; G06T 2207/30101; G06T 2207/30104; G06T 2207/30036; G06T 7/0012; G06T 7/0014; G06T 7/0016; G06T 2207/30088; A61B 5/1172; A61B 5/1174; A61B 5/1176; A61B 5/1178; A61B 5/117; A61B 5/1171; A61B 5/0077; A61B 3/113; A61B 3/14; A61B 5/064; A61B 5/00; A61B 5/112; A61B 5/11; A61B 5/1128; A61B 5/6815; A61B 5/6821; A61B 5/6819; A61B 5/682; A61B 5/6825; A61B 5/6826; A61B 5/1114; H04L 63/0861; H04L 9/3231; H04L 9/0866; H04L 63/08; H04N 23/611; H04N 13/383; B60R 25/25; B60R 25/252; B60R 25/255; B60R 25/257; G06Q 20/40145; G01N 33/48; G01N 33/497; G01N 20/40145; H04W 12/06; A61M 2205/609; G09G 2354/00; G09G 5/003

See application file for complete search history.

(56) References Cited

U.S. PATENT DOCUMENTS

| | | | | |
|---|---|---|---|---|
| 2011/0277518 | A1* | 11/2011 | Lais ................... | G07C 9/10 340/5.83 |
| 2014/0218497 | A1* | 8/2014 | Hanna ................. | G06V 10/242 348/78 |
| 2015/0098629 | A1 | 4/2015 | Perna et al. | |

FOREIGN PATENT DOCUMENTS

| | | |
|---|---|---|
| JP | 2003-308303 A | 10/2003 |
| JP | 2004-030156 A | 1/2004 |
| JP | 2006-019901 A | 1/2006 |
| JP | 2010-009106 A | 1/2010 |
| JP | 2019-078823 A | 5/2019 |
| WO | 2017/070638 A1 | 4/2017 |

OTHER PUBLICATIONS

Extended European Search Report for EP Application No. EP20920411.4 dated on Jan. 27, 2023.
JP Office Action for JP Application No. 2022-501430, mailed on Aug. 15, 2013 with English Translation.
JP Office Action for JP Application No. 2022-501430, mailed on Oct. 17, 2023 with English Translation.
Motonori Doi et al., "A Robust Face Identification against Lighting Fluctuation", Transactions of the Institute of Systems, Control and Information Engineers, Japan, the Institute of Systems, Control and Information Engineers, Oct. 15, 1998, vol. 11, No. 10, pp. 546-553.
International Search Report for PCT Application No. PCT/JP2020/006194, mailed on Apr. 14, 2020.
Written opinion for PCT Application No. PCT/JP2020/006194, mailed on Apr. 14, 2020.
Ministry of Justice, "Operation of Automated Gates (Notice)," [online], [2019]. [retrieved December], Internet URL:http://www.moj.go.jp/nyuukokukanri/kouhou/nyuukokukanri01_00111.html.
"Measures for Safety of IC Passports" described in https://www.mofa.go.jp/mofaj/toko/passport/ic_faq.html#11.

* cited by examiner

FIG. 11

| BODY HEIGHT | LUMINANCE OF UPPER LIGHT | LUMINANCE OF LOWER LIGHT |
|---|---|---|
| A1 cm | B1 cd | C1 cd |
| A2 cm | B2 cd | C2 cd |
| A3 cm | B3 cd | C3 cd |
| ... | ... | ... |

FIG. 12

! ALERT !

PLEASE TAKE YOUR BAGGAGE WITH YOU.

GATE APPARATUS, CONTROL METHOD OF GATE APPARATUS, AND STORAGE MEDIUM

This application is a National Stage Entry of PCT/JP2020/006194 filed on Feb. 18, 2020, the contents of all of which are incorporated herein by reference, in their entirety.

TECHNICAL FIELD

The present invention relates to a gate apparatus, a gate apparatus control method, and a storage medium.

BACKGROUND ART

Emigration and immigration examination is performed at airports. An officer in charge of the emigration and immigration examination compares a photograph of a face attached to a passport with the face of a person in front of the officer. If the face image in the passport does not match the face of the person in front of the officer, the emigration and immigration of the person is not permitted.

In recent years, apparatuses that automatically perform the emigration and immigration examination have been introduced. For example, a gate apparatus disclosed in NPL 1 performs the emigration and immigration examination by comparing previously registered biological information with biological information acquired by the gate apparatus.

CITATION LIST

Non Patent Literature

[NPL 1] Ministry of Justice, "How to use an automated gate (notice)", [online], [search performed in December, 2019], Internet <URL:http://www.moj.go.jp/nyuu-kokukanri/kouhou/nyuukokukanri01_0 0111.html>

SUMMARY OF INVENTION

Technical Problem

As with the gate apparatus disclosed in the above NPL 1, use of face authentication has become available for various kinds of procedures at airports, etc. In a face authentication system, a terminal needs to acquire a face image of a user in front of the terminal. The face authentication terminal needs to acquire a high quality image (face image). That is, to achieve accurate matching, high quality images need to be used as a matching target image and a registered image. For example, if the brightness of one portion is different from the brightness of another portion in an image, this image is not suitable for authentication.

It is a main object of the present invention to provide a gate apparatus, a gate apparatus control method, and a storage medium that contribute to acquiring biological information suitable for authentication.

Solution to Problem

According to a first aspect of the present invention, there is provide a gate apparatus including: an acquisition unit that acquires biological information about a user; an upper light that emits light from above the user; a lower light that emits light from below the user; and a light control unit that changes luminance of the light emitted from the upper light and luminance of the light emitted from the lower light when the biological information about the user is acquired.

According to a second aspect of the present invention, there is provided a control method of a gate apparatus including an upper light that emits light from above a user and a lower light that emits light from below the user, the control method including: changing luminance of the light emitted from the upper light and luminance of the light emitted from the lower light; and acquiring biological information about the user.

According to a third aspect of the present invention, there is provided a computer-readable storage medium storing a program that causes a computer mounted on a gate apparatus including an upper light that emits light from above a user and a lower light that emits light from below the user to perform processing for: changing luminance of the light emitted from the upper light and luminance of the light emitted from the lower light; and acquiring biological information about the user.

Advantageous Effects of Invention

The individual aspects of the present invention provide a gate apparatus, a gate apparatus control method, and a storage medium that contribute to acquiring biological information suitable for authentication. The advantageous effect of the present invention is not limited to the above advantageous effect. The present invention may provide other advantageous effects, instead of or in addition to the above advantageous effect.

BRIEF DESCRIPTION OF THE DRAWINGS

FIG. 11 is a diagram illustrating an example of table information in which body heights and luminances of two light sources are defined.

FIG. 12 is a diagram illustrating an example of an alert message about left-behind baggage.

EXAMPLE EMBODIMENT

Figure 1:
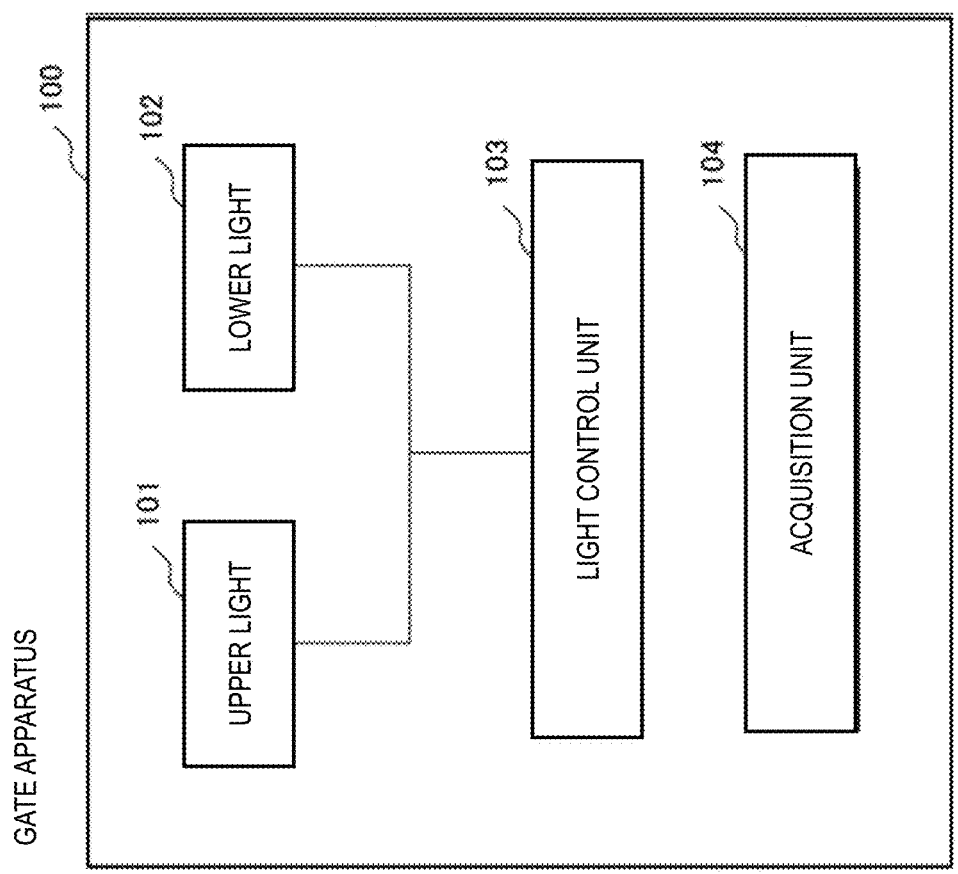
FIG. 1 is a diagram illustrating an outline of an example embodiment.

First, an outline of an example embodiment will be described. In the following outline, various components are denoted by reference characters for the sake of convenience. That is, the following reference characters are used as examples to facilitate the understanding of the present invention. Thus, the description of the outline is not intended to impose any limitations. In addition, unless otherwise specified, an individual block illustrated in the drawings represents a configuration of a functional unit, not a hardware unit. An individual connection line between blocks in the drawings signifies both one-way and two-way directions. An arrow schematically illustrates a principal signal (data) flow and does not exclude bidirectionality. In the present description and drawings, elements that can be described in a like way will be denoted by a like reference character, and redundant description thereof will be omitted as needed.

A gates apparatus 100 according to an example embodiment includes an upper light 101 that emits light from above a user, a lower light 102 that emits light from below the user, a light control unit 103, and an acquisition unit 104. The acquisition unit 104 acquires biological information about the user. The light control unit 103 changes the luminance of the light emitted from the upper light 101 and the luminance of the light emitted from the lower light 102 when the biological information about the user is acquired.

When acquiring the biological information about the user (for example, a face image or an iris image), the gate apparatus 100 controls the luminance of the light emitted from the upper light 101 and the luminance of the light emitted from the lower light 102. For example, the gate apparatus 100 changes the luminance of the light emitted from the upper light 101 and the luminance of the light emitted from the lower light 102 such that the user is illuminated with light with uniform illuminance. Specifically, the gate apparatus 100 controls the two light sources such that, for example, the face of the user is illuminated with light with uniform brightness. As a result, biological information suitable for authentication is acquired.

Hereinafter, a specific example embodiment will be described in more detail with reference to the drawings.

First Example Embodiment

A first example embodiment will be described in more detail with reference to drawings.

[System Configuration]

Figure 2:
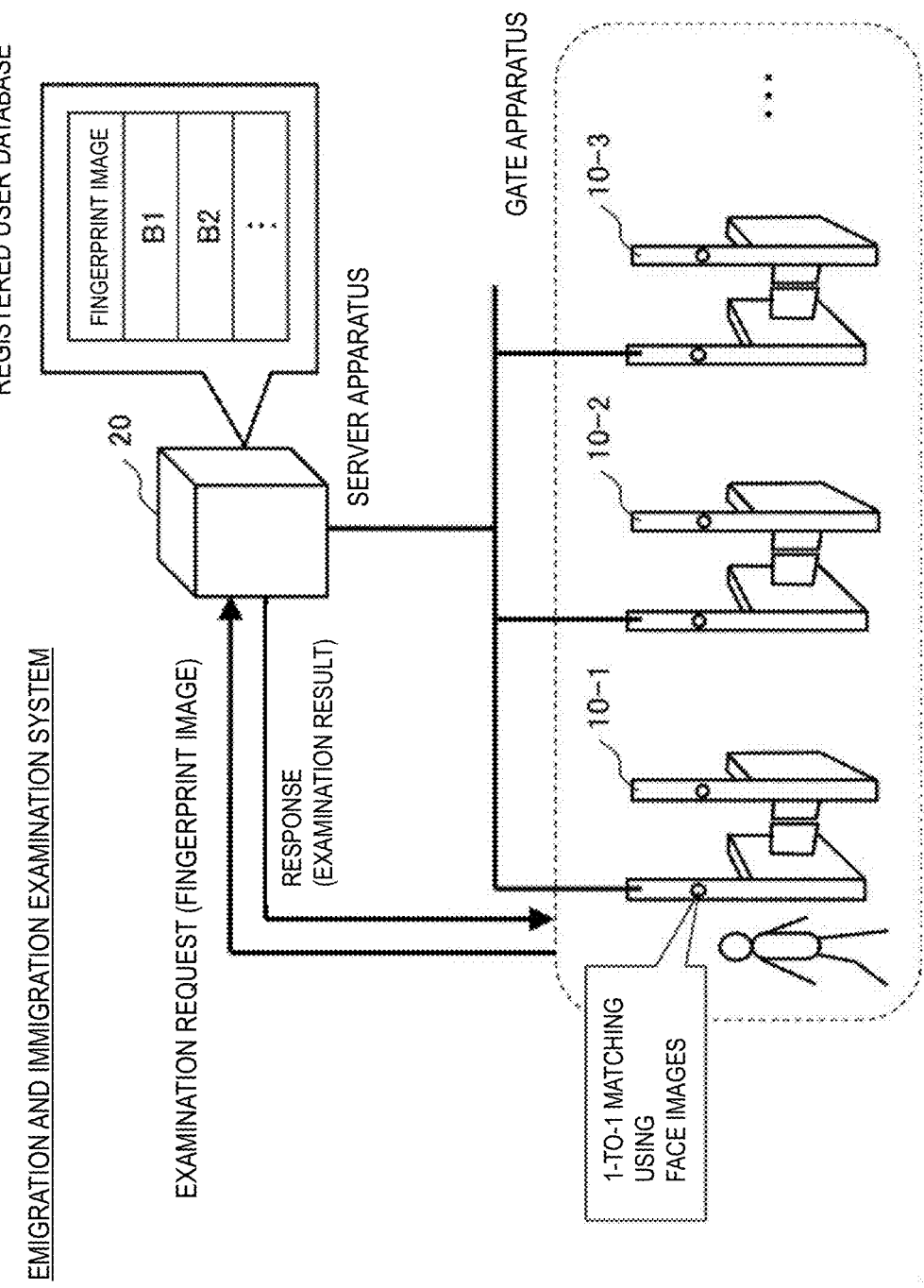
FIG. 2 is a diagram illustrating an example of a schematic configuration of an emigration and immigration examination system according to the first example embodiment.

FIG. 2 is a diagram illustrating an example of a schematic configuration of an emigration and immigration examination system according to the first example embodiment. As illustrated in FIG. 2, the emigration and immigration examination system includes a plurality of gate apparatuses 10-1 to 10-3 and a server apparatus 20. In the following description, unless there is a particular reason to distinguish the gate apparatuses 10-1 to 10-3 from each other, any one of these gate apparatuses 10-1 to 10-3 will simply be referred to as a "gate apparatus 10". In addition, while three gate apparatuses 10 are illustrated in FIG. 2, the number of gate apparatuses 10 included in the system is not of course limited to any particular number. The emigration and immigration examination system includes at least one gate apparatus 10.

The individual gate apparatus 10 and the server apparatus 20 can communicate with each other via wired or wireless communication means. The server apparatus 20 may be installed in the same airport where the gate apparatuses 10 are installed. Alternatively, the server apparatus 20 may be installed on a network (cloud).

The individual gate apparatus 10 is an apparatus that automatically performs emigration and immigration examination procedures for users. The gate apparatus 10 includes a gate that can be opened and closed. If the gate apparatus 10 determines that a person standing in front of the gate apparatus 10 has passed the emigration and immigration examination and that the person possesses a correct passport, the gate apparatus 10 opens the gate and allows the user to pass through the gate. Thus, the gate apparatus 10 controls the gate based on the result of the emigration and immigration examination of the user.

The server apparatus 20 is an apparatus that realizes the emigration and immigration examination with the above gate apparatus 10. The server apparatus 20 stores information about users who can use the gate apparatus 10 (the information will hereinafter be referred to as gate user information).

Users who wish to use the automatic examination with the gate apparatus 10 need to previously register themselves in the system. For example, a user visits a passport center and presents his or her passport to an officer in charge at the passport center. The person in charge examines whether the user who has presented the passport is truly the owner of the passport. As a result of the examination, if the person in charge determines that the user is the correct owner of the passport, the person in charge acquires a fingerprint image of the user. Specifically, the person in charge acquires a fingerprint image of the user by using a fingerprint scanner or the like. This fingerprint image is entered to the server apparatus 20.

The server apparatus 20 adds the acquired fingerprint image to a database (which will hereinafter be referred to as a registered user database). The fingerprint image to be registered is a fingerprint image obtained from at least one finger. In addition to the fingerprint image of the user who has passed the examination, other information (for example, the name and passport number) may be registered in the registered user database in association with the fingerprint image. Alternatively, feature values (kinds and locations of feature points, for example) necessary for matching processing using the fingerprint image may be registered in the registered user database in association with the fingerprint image.

[Outline of System Operation]

Next, a schematic operation of the emigration and immigration examination system according to the first example embodiment will be described with reference to FIG. 2.

When a user stands in front of a gate apparatus 10, the user places his or her finger on a scanner in accordance with an instruction given by the gate apparatus 10. The gate apparatus 10 acquires a fingerprint image of the user and transmits an examination request including the acquired fingerprint image to the server apparatus 20.

The server apparatus 20 performs matching processing (1-to-N matching processing; N will hereinafter denote a positive integer) by using the acquired fingerprint image and a plurality of fingerprint images registered in the registered user database. If a fingerprint image that substantially matches the acquired fingerprint image is registered in the registered user database, the server apparatus 20 sets the examination result to "emigration and immigration permitted".

However, if no fingerprint image that substantially matches the acquired fingerprint image is registered in the registered user database, the server apparatus 20 sets the examination result to "emigration and immigration not permitted". The server apparatus 20 transmits the examination result to the gate apparatus 10 that has transmitted the examination request.

After receiving the examination result or after transmitting the examination request, the gate apparatus 10 determines whether the user in front of the gate apparatus 10 possesses a correct passport (his or her own passport). Specifically, the gate apparatus 10 instructs the user to open and place his or her passport on a scanner. The gate apparatus 10 reads out a face image or the like from an IC (Integrated Circuit) chip in the passport by using a card reader function of the scanner. The gate apparatus 10 acquires a face image of the user by using a camera device. The gate apparatus 10 generates feature values (hereinafter, face feature values) from each of the two face images and determines whether the two sets of feature values substantially match. That is, the gate apparatus 10 performs 1-to-1 matching by using the face feature values obtained by capturing an image of the user in front of the gate apparatus 10 and the face feature values obtained from the IC chip in the passport.

If the 1-to-1 matching succeeds and the examination result obtained by the server apparatus 20 indicates "emigration and immigration permitted", the gate apparatus 10 opens the gate and allows the user to pass through the gate.

Next, the individual apparatuses included in the emigration and immigration examination system according to the first example embodiment will be described in detail.

[Server Apparatus]

Figure 3:
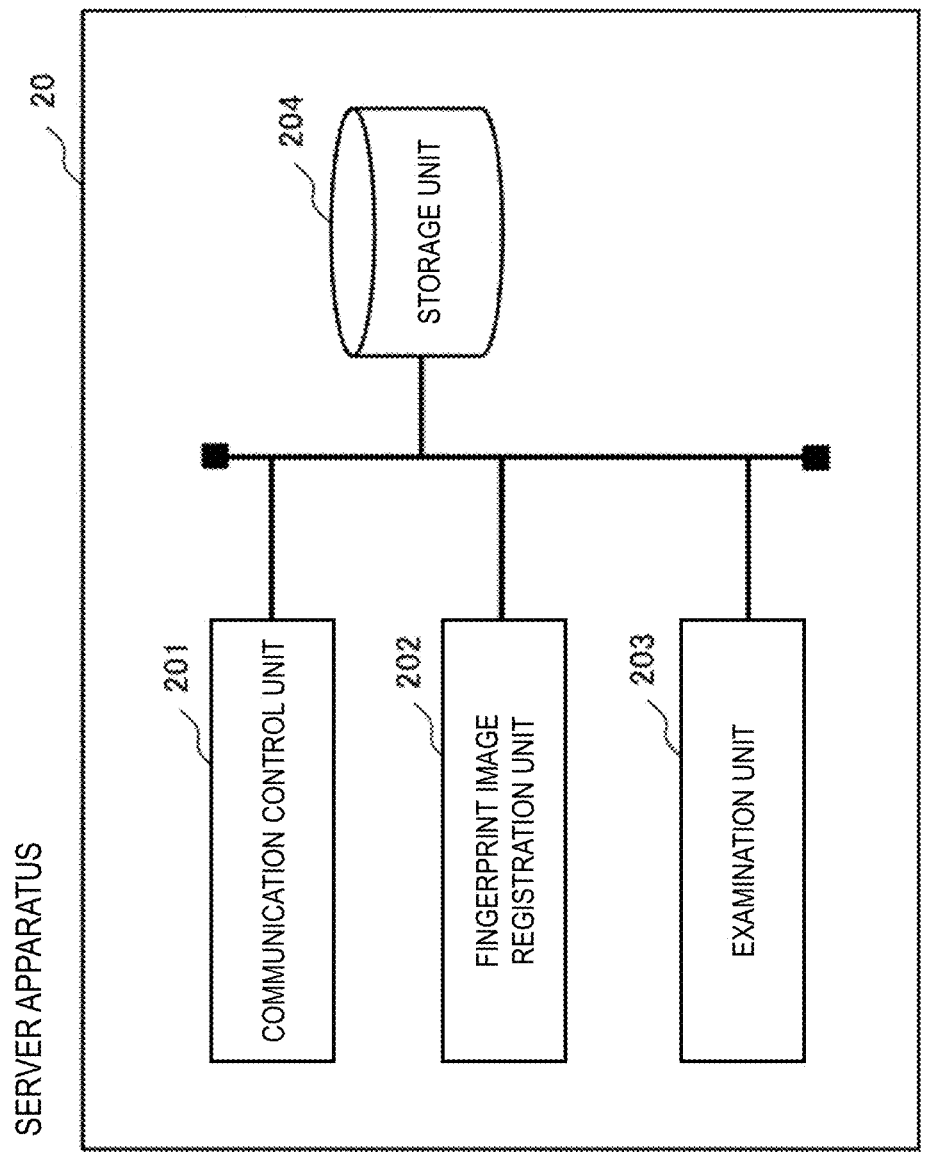
FIG. 3 is a diagram illustrating an example of a processing configuration of a server apparatus according to the first example embodiment.

FIG. 3 is a diagram illustrating an example of a processing configuration (processing modules) of the server apparatus 20 according to the first example embodiment. As illustrated in FIG. 3, the server apparatus 20 includes a communication control unit 201, a fingerprint image registration unit 202, an examination unit 203, and a storage unit 204.

The communication control unit 201 is means for controlling communication with other apparatuses. Specifically, the communication control unit 201 receives data (packets) from a gate apparatus 10. In addition, the communication control unit 201 transmits data to a gate apparatus 10.

The fingerprint image registration unit 202 is means for registering acquired fingerprint images in the registered user database configured in the storage unit 204. The method for acquiring fingerprint images is not limited to any particular method.

For example, an officer in charge at a passport center may enter a fingerprint image in the server apparatus 20. Specifically, an officer in charge operates a fingerprint scanner to acquire a fingerprint image of a user. The officer in charge operates a terminal (a computer installed at the passport center) to transmit the acquired fingerprint image to the server apparatus 20. Alternatively, the above read data may be entered to the server apparatus 20 via an external storage device, such as a USB (Universal Serial Bus) memory.

The examination unit 203 is means for processing examination requests transmitted by the gate apparatuses 10. Specifically, the examination unit 203 sets a fingerprint image (biological information) included in an examination request as the matching target fingerprint image and performs matching processing between this fingerprint image and the fingerprint images registered in the registered user database.

More specifically, the examination unit 203 sets a fingerprint image extracted from an examination request as the matching target fingerprint image and performs 1-to-N matching between this fingerprint image and the plurality of fingerprint images registered in the registered user database. The examination unit 203 calculates a score (similarity) between the fingerprint image as the matching target fingerprint image and each of the plurality of fingerprint images registered.

The examination unit 203 extracts feature points (edge points, branch points) from each of the matching target fingerprint image and the registered fingerprint images. The examination unit 203 calculates a score indicating a similarity between two fingerprint images, based on the extracted feature points, etc. Specifically, the examination unit 203 matches the core area of one fingerprint image (the center area of one fingerprint) with the core area of another fingerprint image (the center area of another fingerprint) and calculates the above score, for example, based on the locations of and the number of feature points seen from each core area and the number of core lines present between feature points. A higher score represents a higher similarity between two fingerprint images.

Existing techniques can be used to extract feature points from the fingerprint images and to calculate scores from the feature points. Since these techniques are apparent to those skilled in the art, further description thereof will be omitted.

The examination unit 203 determines whether at least one of the plurality of fingerprint images registered in the registered user database indicates a score more than or equal to a predetermined value with respect to the matching target fingerprint image.

If a fingerprint image indicating a score more than or equal to a predetermined value is present in the registered user database, the examination unit 203 sets the examination result to "emigration and immigration permitted". However, if a fingerprint image indicating a score more than or equal to a predetermined value is not present in the registered user database, the examination unit 203 sets the examination result to "emigration and immigration not permitted". The examination unit 203 transmits the examination result to the gate apparatus 10 that has transmitted the examination request.

The storage unit 204 stores various kinds of information necessary for the operation of the server apparatus 20. In addition, the registered user database is configured in the storage unit 204.

Figure 4:
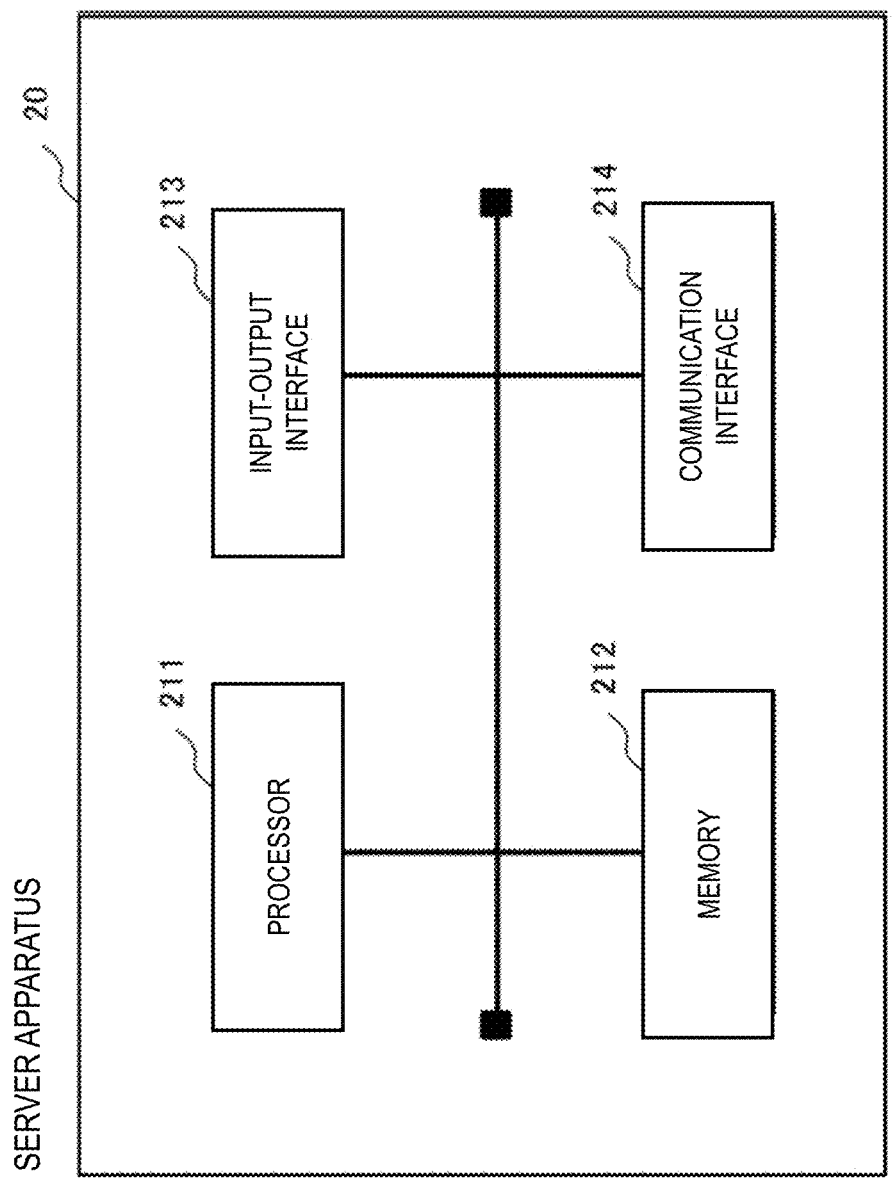
FIG. 4 is a diagram illustrating an example of a hardware configuration of the server apparatus according to the first example embodiment.

FIG. 4 is a diagram illustrating an example of a hardware configuration of the server apparatus 20 according to the first example embodiment. The server apparatus 20 can be configured by an information processing apparatus (a so-called computer) and has a configuration illustrated as an example in FIG. 4. For example, the server apparatus 20 includes a processor 211, a memory 212, an input-output interface 213, a communication interface 214, etc. The components such as the processor 211 are connected to an internal bus or the like so that these components can communicate with each other.

The hardware configuration of the server apparatus 20 is not limited to the configuration illustrated in FIG. 4. The server apparatus 20 may include hardware not illustrated or may be configured without the input-output interface 213 if desired. In addition, the number of components, such as the number of processors 211, included in the server apparatus 20 is not limited to the example illustrated in FIG. 4. For example, a plurality of processors 211 may be included in the server apparatus 20.

For example, the processor 211 is a programmable device such as a CPU (Central Processing Unit), an MPU (Micro Processing Unit), or a DSP (Digital Signal Processor). Alternatively, the processor 211 may be a device such as an FPGA (Field Programmable Gate Array) or an ASIC (Application Specific Integrated Circuit). The processor 211 executes various kinds of programs including an operating system (OS).

The memory 212 is a RAM (Random Access Memory), a ROM (Read-Only Memory), an HDD (Hard Disk Drive), an SSD (Solid State Drive), or the like. The memory 212 stores an OS program, application programs, and various kinds of data.

The input-output interface 213 is an interface for a display apparatus and an input apparatus not illustrated. For example, the display apparatus is a liquid crystal display or the like. For example, the input apparatus is an apparatus that receives user operations, and examples of the input apparatus include a keyboard and a mouse.

The communication interface 214 is a circuit, a module, or the like for performing communication with other apparatuses. For example, the communication interface 214 includes a NIC (Network Interface Card) or the like.

The functions of the server apparatus 20 are realized by various kinds of processing modules. The processing modules are realized, for example, by causing the processor 211 to execute a program stored in the memory 212. In addition, this program can be recorded in a computer-readable storage medium. The storage medium may be a non-transient (non-transitory) storage medium, such as a semiconductor memory, a hard disk, a magnetic recording medium, or an optical recording medium. That is, the present invention can be embodied as a computer program product. In addition, the above program may be updated by downloading a program via a network or by using a storage medium in which a program is stored. In addition, the above processing modules may be realized by semiconductor chips.

[Gate Apparatus]

Figure 5:
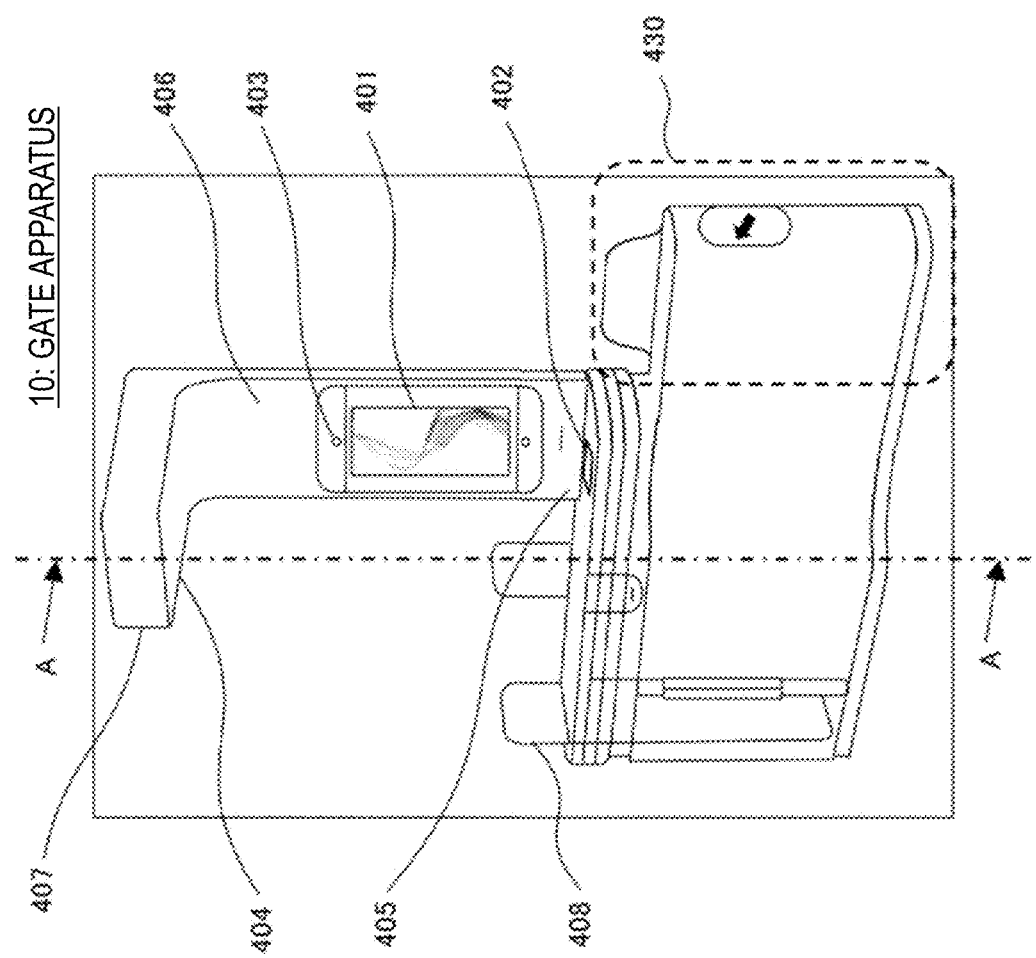
FIG. 5 is a diagram illustrating an example of the exterior of a gate apparatus according to the first example embodiment.

FIG. 5 is a diagram illustrating an example of the exterior of a gate apparatus 10 according to the first example embodiment. As described above, the individual gate apparatus 10 is an apparatus that automatically performs the emigration and immigration examination for users.

If a gate apparatus 10 detects presence of a user in front of the gate apparatus 10, for example, the gate apparatus 10 displays, on a display 401, a procedure of an operation that the user needs to perform for the automatic emigration and immigration examination.

The gate apparatus 10 instructs the user to place his or her finger (a predetermined finger; a finger corresponding to the fingerprint image registered in the registered user database) on a scanner 402. The gate apparatus 10 captures an image of the placed finger by controlling the scanner 402. The gate apparatus 10 transmits an examination request including the obtained fingerprint image to the server apparatus 20.

After acquiring the fingerprint image, the gate apparatus 10 notifies the user that an image of the face of the user needs to be captured and captures an image of the face of the user by controlling a camera device 403. At this point, the gate apparatus 10 controls the luminance of an upper light 404 attached to a location above the user and the luminance of lower light 405 attached to a location below the user.

The upper light 404 is installed in a ceiling portion 407 attached to a supporting portion 406 extending vertically upward from the main body of the gate apparatus 10. More specifically, the upper light 404 is embedded into the ceiling portion 407. As illustrated in FIG. 5, since the supporting portion 406 is structured to have a wide width, the display 401 or the camera device 403 can be attached to the supporting portion 406.

The lower light 405 is embedded into the main body of the gate apparatus 10. The "main body" of the gate apparatus 10 is a structure that forms the core of the gate apparatus 10. This main body is into contact with the floor, and a gate 408 and the supporting portion 406 are attached to the main body.

Figure 6:
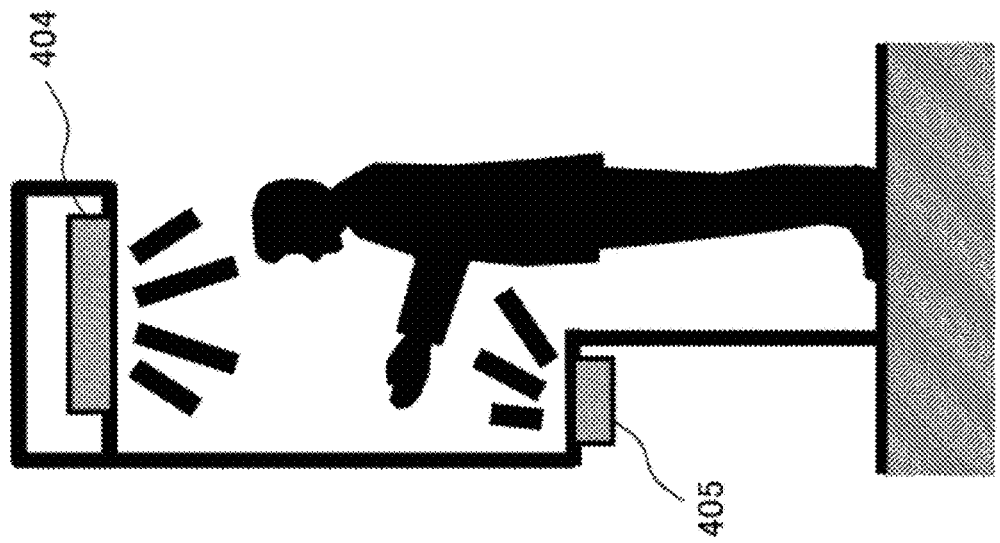
FIG. 6 is a diagram schematically illustrating a cross section of the gate apparatus according to the first example embodiment.

FIG. 6 is a diagram schematically illustrating a cross section of the gate apparatus 10, taken along a line A-A in FIG. 5. To facilitate understanding of the description, a user (an examination target user) of the gate apparatus 10 is illustrated in FIG. 6. As illustrated in FIG. 6, the upper light 404 is installed such that light is emitted to the user from above the user. In addition, the lower light 405 is installed such that light is emitted to the user from below the user (more specifically, from below the face of the user).

The arrangement of the two lights illustrated in FIG. 6 is only an example, and therefore, various modifications are possible. For example, the upper light 404 may be installed on the supporting portion 406. Alternatively, the upper light 404 may be installed on the supporting portion 406 and attached to emit light toward the ceiling portion 407. In this case, a reflective plate (for example, a mirror) may be disposed on the ceiling portion 407 such that the light emitted from the upper light 404 is reflected by the mirror and the user is illuminated with the reflected light from above the user. Thus, the upper light 404 may be installed to emit light toward the ceiling portion 407, and the gate apparatus 10 may include a reflective plate that reflects the light emitted from the upper light 404.

Likewise, the lower light 405 may be installed on a lower part of the supporting portion 406. Alternatively, the lower light 405 may be installed to emit light to a mirror attached to the main body of the gate apparatus 10. In this case, the light emitted from the lower light 405 is reflected by the mirror, and the user is illuminated with the reflected light from below the user. Thus, the lower light 405 may be installed to emit light toward the main body of the gate apparatus 10, and the gate apparatus 10 may include a reflective plate that reflects the light emitted from the lower light 405.

The gate apparatus 10 controls the luminances of the above two lights such that a face image suitable for matching processing using face images to be described below can be acquired. Details of the light control performed by the gate apparatus 10 will be described below.

After capturing an image of the user, the gate apparatus 10 extracts a face area from the image and acquires a face image.

In addition, the gate apparatus 10 instructs the user to open his or her passport to the page including a photograph of the face of the user and places the open passport on the scanner 402. The gate apparatus 10 reads out information (hereinafter, MRZ information) written in a Machine Readable Zone (MRZ) in the passport. The gate apparatus 10 acquires a face image stored in an IC chip in the passport by using the MRZ information.

The gate apparatus 10 performs matching (1-to-1 matching) between the face image acquired from the camera device 403 and the face image acquired from the IC chip in the passport. If the matching succeeds (if the two face images substantially match), the gate apparatus 10 determines that the user possesses a correct passport. However, if the matching fails (if the two face images are different), the gate apparatus 10 determines that the user does not possess a correct passport.

If the examination result from the server apparatus 20 indicates "emigration and immigration permitted" and the gate apparatus 10 determines that the user possesses a correct passport, the gate apparatus 10 opens the gate 408 and allows the user (the examination target user) to pass through the gate 408.

If the examination result from the server apparatus 20 indicates "emigration and immigration not permitted" or the gate apparatus 10 determines that "the user does not possess a correct passport", the gate apparatus 10 keeps the gate 408 closed and displays a predetermined message or the like on the display 401. For example, the gate apparatus 10 displays a message requesting the user to go to a staffed examination booth or to operate the gate apparatus 10 for the automatic examination again.

Figure 7:
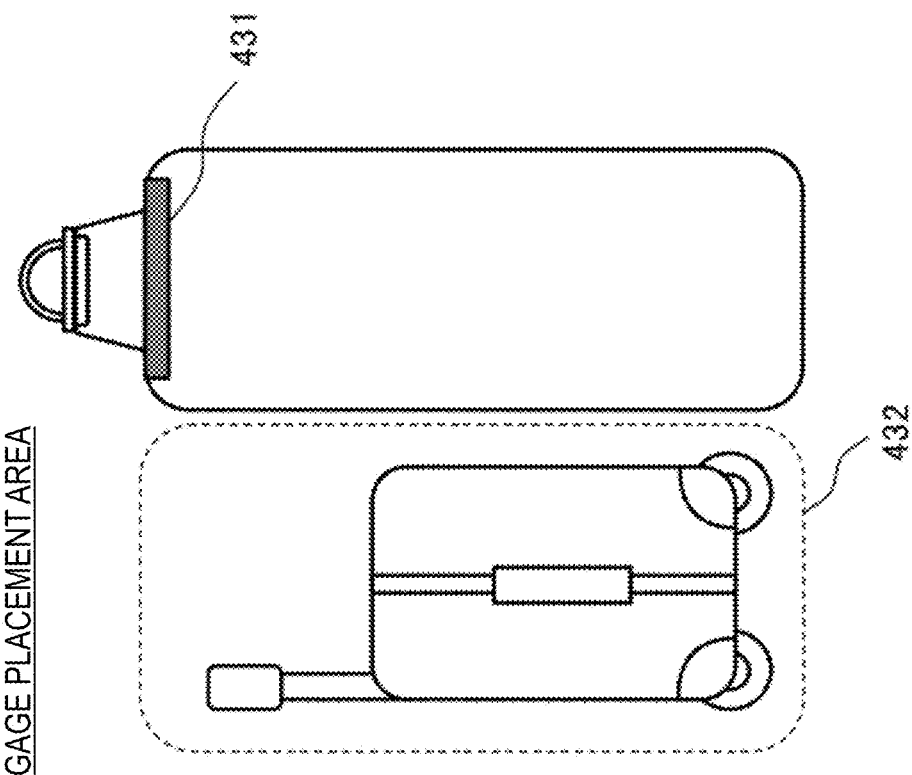
FIG. 7 is an example of a front view schematically illustrating a baggage placement area of the gate apparatus according to the first example embodiment.

The gate apparatus 10 monitors the state of a baggage placement area 430. FIG. 7 is an example of a front view schematically illustrating the baggage placement area 430 of the gate apparatus 10. FIG. 7 is a diagram of the baggage placement area 430 seen from the direction in which the user walks toward the gate apparatus 10.

When operating the gate apparatus 10, the user places his or her baggage on a top board area 431 or a side area 432 of the baggage placement area 430. The gate apparatus 10 detects whether there is an object on the top board area 431 or the side area 432. For example, the gate apparatus 10 detects an object placed on the top board area 431 by using means such as a weight sensor or a pressure sensor. Alternatively, the gate apparatus 10 detects an object placed on the side area 432 by using a distance sensor using infrared light or by analyzing an image obtained from a camera.

The above object detection method of the gate apparatus 10 is only an example. The gate apparatus 10 may use any method or means to detect an object placed in the baggage placement area 430. In addition, the object (user's baggage) detection area of the gate apparatus 10 is not limited to the top board area 431 and the side area 432. Any areas where users may place their baggage may be set as the detection areas. That is, the gate apparatus 10 not only detects presence of objects located on the area vertically upward of the baggage placement area 430 and the side area but also detects presence of objects located at other areas where users may place their baggage.

If the gate apparatus 10 detects presence of an object in the baggage placement area 430, the gate apparatus 10 sets a "baggage detection flag" to "1". If the gate apparatus 10 no longer detects the object in the baggage placement area 430, the gate apparatus 10 clears the "baggage detection flag" to "0".

Upon completion of the emigration and immigration examination on a user (when the gate apparatus 10 has received an examination result and completes the passport possession determination), if "1" is set as the baggage detection flag, the gate apparatus 10 notifies (alerts) the user about his or her left-behind baggage in the baggage placement area 430. For example, the gate apparatus 10 may display an alert message on the display 401 or may output a sound or the like as an alert.

Regarding the opening and closing control of the gate 408, one of the conditions for the gate apparatus 10 to open the gate 408 is that the baggage detection flag has been cleared to "0". Even when the user does not notice the display or sound alerting the user about his or her left-behind baggage, since the gate 408 remains closed, the user is prevented from proceeding to the next procedure without his or her baggage.

Figure 8:
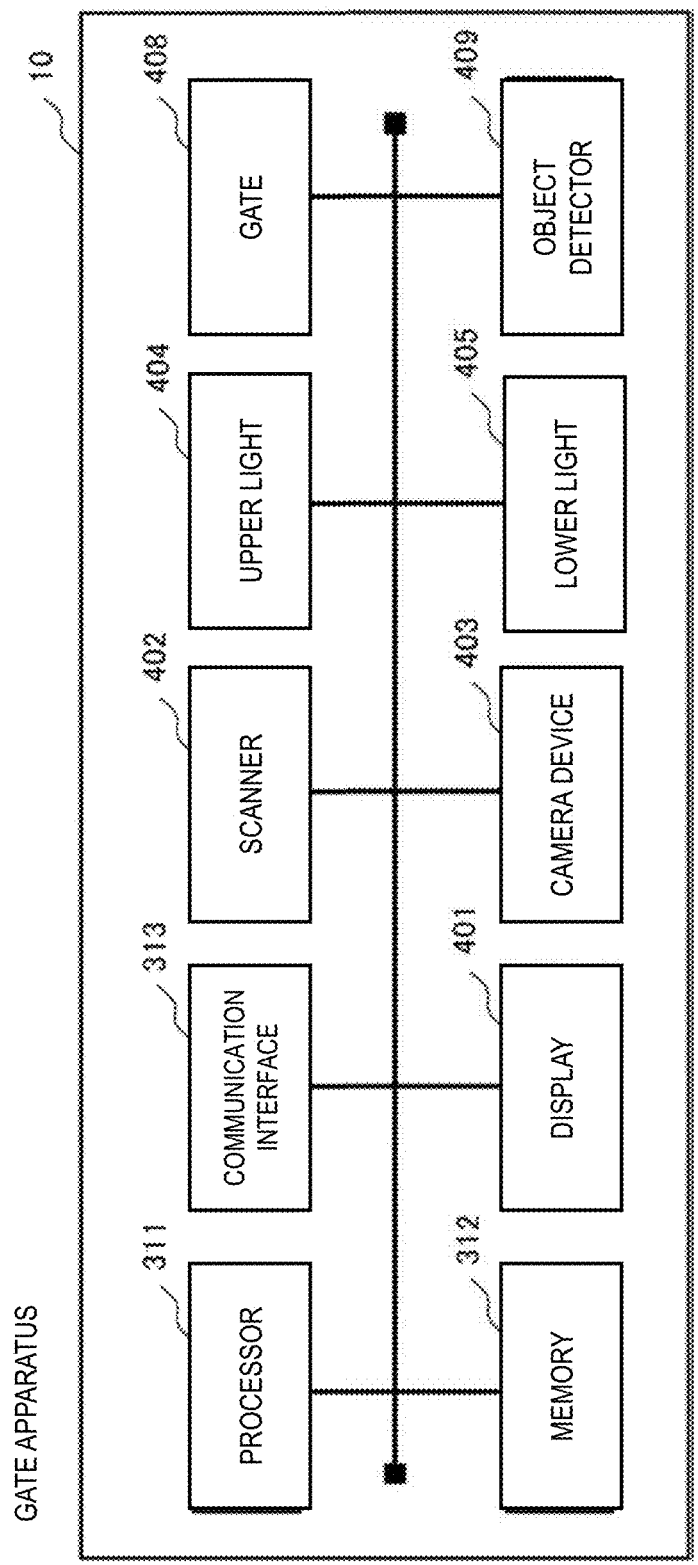
FIG. 8 is a diagram illustrating an example of a hardware configuration of the gate apparatus according to the first example embodiment.

FIG. 8 is a diagram illustrating an example of a hardware configuration of the individual gate apparatus 10 according to the first example embodiment. As illustrated in FIG. 8, the gate apparatus 10 includes a processor 311, a memory 312, and a communication interface 313. In addition, the gate apparatus 10 includes a display 401, a scanner 402, a camera device 403, an upper light 404, a lower light 405, a gate 408, and an object detector 409. These components such as the processor 311 are connected to an internal bus or the like and configured to communicate with each other. FIG. 8 illustrates only the components connected (electrically connected) to the processor 311. In FIG. 8, the supporting portion 406, the ceiling portion 407, and the baggage placement area 430 are not illustrated. In addition, as illustrated in FIG. 5, the main body of the gate apparatus, the supporting portion 406, and the ceiling portion 407 are formed in the shape of the letter C. More specifically, the main body of the gate apparatus 10 (the housing that supports the supporting portion 406) faces the ceiling portion 407. The main body and the ceiling portion 407 are connected to each other by the supporting portion 406. Since the gate apparatus 10 is structured in this way, the main body, the supporting portion 406, and the ceiling portion 407 are formed in the shape of the letter C (specifically, a mirror symmetry of the letter "c").

Since the processor 311, the memory 312, and the communication interface 313 are equivalent to those of the server apparatus 20 described with reference to FIG. 4, detailed description thereof will be omitted.

The display 401 is a device (for example, a liquid crystal monitor or the like) for outputting information.

The scanner 402 is a device that reads out MRZ information from passports and acquires fingerprint images of users. The scanner 402 also has a function of accessing IC chips in passports. The scanner 402 may be installed at any location of the gate apparatus 10. However, it is preferable that the scanner 402 be installed at a location where users can easily place their passports or fingers. The present application will be described assuming that the scanner 402 has a function as a card reader that accesses IC chips, a function as a passport scanner that reads out MRZ information from passports, and a function as a fingerprint scanner that acquires fingerprint images from fingers. However, these functions may be separated from each other. That is, a card reader, a passport scanner, and a fingerprint scanner may be installed separately in the gate apparatus 10.

For example, the camera device 403 is a digital camera installed to capture an image of a person in front of the gate apparatus 10. The camera device 403 may be installed at any location. For example, the camera device 403 may be installed on the main body of the gate apparatus 10 or may be installed away from the gate apparatus 10. As long as the camera device 403 can capture an image of a user (in particular, the face of a user) in front of the gate apparatus 10, the camera device 10 may be installed at any location.

As described above, the upper light 404 is a light source installed to emit light to the user from above the user. The lower light 405 is a light source installed to emit light to the user from below the user. The luminance of the upper light 404 and the luminance of the lower light 405 are variable. Since the luminance of the upper light 404 and the luminance of the lower light 405 are variable, the illuminance of the light emitted to the user varies. That is, since the luminance of the upper light 404 and the luminance of the lower light 405 are varied, the brightness of the user seen from the camera device 403 varies. Any light source of which luminance is variable may be used as each of the upper light 404 and the lower light 405. For example, an LED (Light Emitting Diode) may be used as each of the upper light 404 and the lower light 405. If an LED is used as a light source, the luminance can be changed by controlling the current flowing through the LED.

After the user passes the emigration and immigration examination, the gate 408 shifts from its standby closed state that blocks passage of the user to its open state that allows passage of the user. The mechanism of the gate 408 is not limited to any particular mechanism. For example, the gate 408 is a flap gate that opens and closes a flap installed on one side or flaps installed on both sides of the passage or is a turnstile gate that rotate three bars.

The object detector 409 is a device for detecting an object placed in the baggage placement area 430. As described above, a weight sensor, a distance sensor, or the like may be used as the object detector 409.

As is the case with the server apparatus 20, the functions of the gate apparatus 10 are realized by various kinds of processing modules. The processing modules are realized by, for example, causing the processor 311 to execute a program stored in the memory 312.

Figure 9:
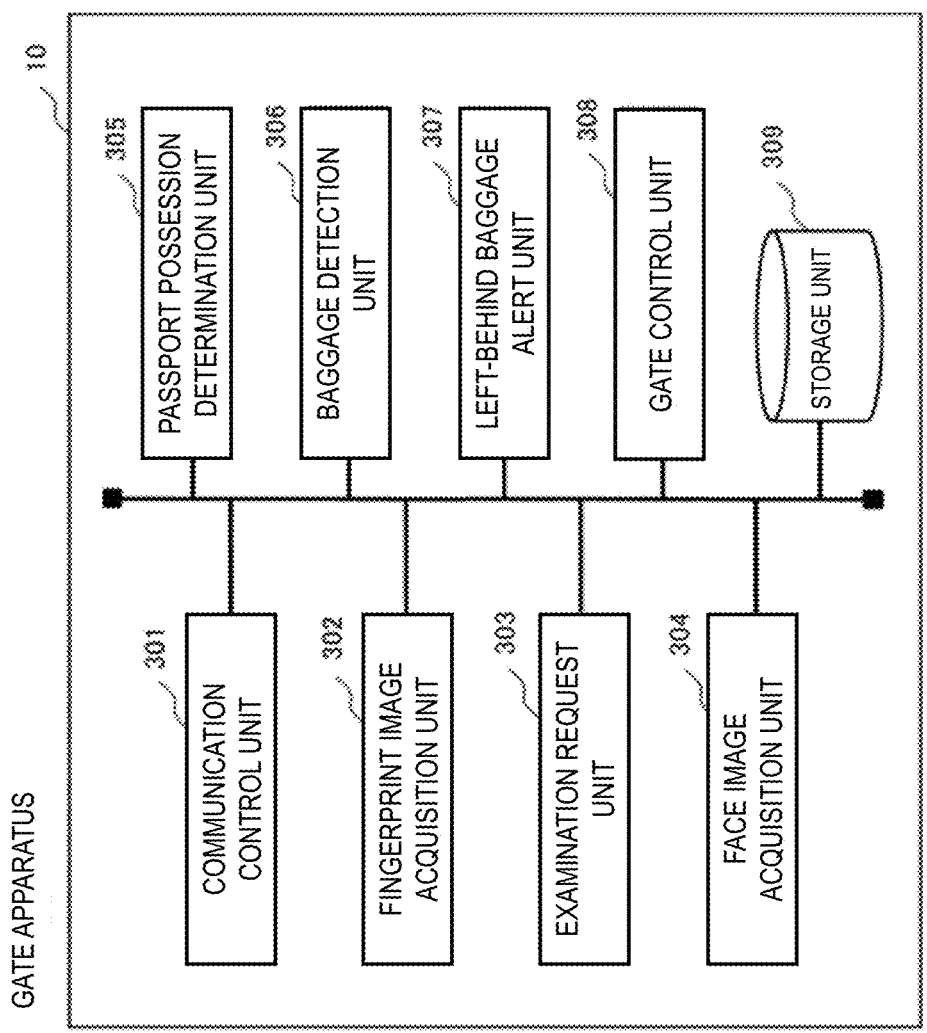
FIG. 9 is a diagram illustrating an example of a processing configuration of the gate apparatus according to the first example embodiment.

FIG. 9 is a diagram illustrating an example of a processing configuration (processing modules) of the individual gate apparatus 10 according to the first example embodiment. The gate apparatus 10 includes a communication control unit 301, a fingerprint image acquisition unit 302, an examination request unit 303, a face image acquisition unit 304, a passport possession determination unit 305, a baggage detection unit 306, a left-behind baggage alert unit 307, a gate control unit 308, and a storage unit 309.

The communication control unit 301 is means for controlling communication with other apparatuses. Specifically, the communication control unit 301 receives data (packets) from the server apparatus 20. In addition, the communication control unit 301 transmits data to the server apparatus 20.

The fingerprint image acquisition unit 302 is means for acquiring a fingerprint image of a user standing in front of the gate apparatus 10. The fingerprint image acquisition unit 302 acquires a fingerprint image of a user by controlling the scanner 402. The fingerprint image acquisition unit 302 gives the acquired fingerprint image to the examination request unit 303.

The examination request unit 303 is means for requesting the server apparatus 20 to perform the emigration and immigration examination on the examination target user (the user standing in front of the gate apparatus 10). Specifically, the examination request unit 303 generates an examination request including the acquired fingerprint image (biological information) and transmits the generated examination request to the server apparatus 20 via the communication control unit 301.

Figure 10:
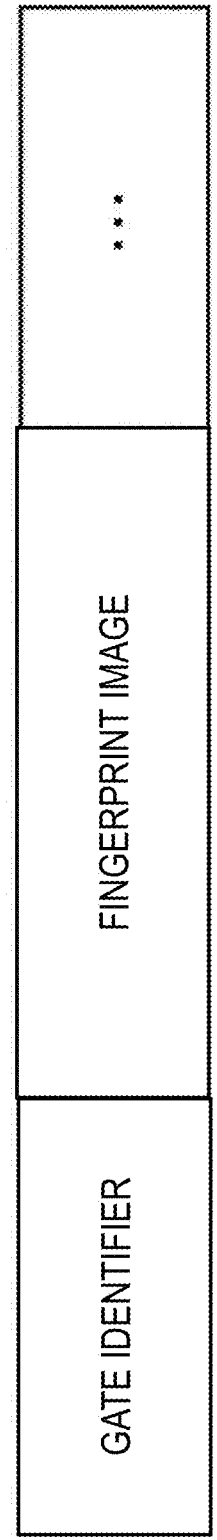
FIG. 10 is a diagram illustrating an example of an examination request.

For example, the examination request unit 303 generates an examination request including an identifier of this gate apparatus 10 (hereinafter referred to as a gate identifier), a fingerprint image, etc. (see FIG. 10). A MAC (Media Access Control) address or an IP (Internet Protocol) address of the gate apparatus 10 may be used as the gate identifier.

The examination request unit 303 receives a response to the examination request from the server apparatus 20 via the communication control unit 301. The examination request unit 303 gives the response (an examination result; emigration and immigration permitted or emigration and immigration not permitted) from the server apparatus 20 to the left-behind baggage alert unit 307 and the gate control unit 308.

The face image acquisition unit 304 is means for acquiring a face image (biological information) of the user standing in front of the gate apparatus 10. For example, the face image acquisition unit 304 acquires a face image of the user by controlling the camera device 403. The face image acquisition unit 304 gives the acquired face image to the passport possession determination unit 305.

As described above, when capturing an image of the user, the gate apparatus 10 controls the luminance of the upper light 404 and the luminance of the lower light 405. Specifically, the face image acquisition unit 304 controls the luminance of the upper light 404 and the luminance of the lower light 405 such that the face of the user is illuminated with light with substantially uniform illuminance when an image of the face of the user is captured. As long as the above uniform illuminance can be achieved, the face image acquisition unit 304 may control the luminance of only one of the upper light 404 and the lower light 405. The face image acquisition unit 304 has a function as a light control unit that controls at least two lights and a function as an acquisition unit that acquires biological information about users.

For example, the face image acquisition unit 304 determines the luminance of the upper light 404 and the luminance of the lower light 405 based on a physical feature of a user (a user to be photographed). For example, if the body height of the user is high (if the body height of the user is higher than a first threshold), the face image acquisition unit 304 sets the luminance of the lower light 405 to be higher than the luminance of the upper light 404. In contrast, if the body height of the user is low (if the body height of the user is lower than a second threshold), the face image acquisition unit 304 sets the luminance of the upper light 404 to be higher than the luminance of the lower light 405. If the body height of the user falls within a range determined by the first and second thresholds (if the user has an average body height), the face image acquisition unit 304 may set the luminance of the upper light and the luminance of the lower light to be the same. The face image acquisition unit 304 controls the luminance of the upper light 404 and the luminance of the lower light 405 as described above such that the user is illuminated with light with uniform illuminance when an image of the user is captured.

To achieve the above uniform illuminance, first, the face image acquisition unit 304 measures the body height of the user. Next, the face image acquisition unit 304 refers to table information in which body heights and luminances of the two light sources are defined in advance. The face image acquisition unit 304 controls the upper light 404 and the lower light 405 such that the necessary luminances can be obtained from the table information.

FIG. 11 is a diagram illustrating an example of table information in which body heights and luminances of the two light sources are defined. The face image acquisition unit 304 acquires the luminance of the upper light 404 and the luminance of the lower light 405 based on the body height of the user. The face image acquisition unit 304 controls a current flowing through the upper light 404 and a current flowing through the lower light 405 such that the upper light 404 and the lower light 405 emit light with their respective luminances acquired. When the current values are determined from their respective luminances, the face image acquisition unit 304 may use table information in which these relationships are defined in advance or may use a function (a function that outputs current values when receiving luminances). When the current value of a light source is set to be variable, a resistor connected between the light source and a power supply may be changed. Alternatively, a voltage applied to the light source may be changed by using a PWM (Pulse Width Modulation) technique or the like.

The face image acquisition unit 304 acquires the body height of the user in accordance with any method. For example, a plurality of sensors (for example, infrared distance sensors) are disposed vertically on the supporting portion 406 of the gate apparatus 10. More specifically, the plurality of sensors are disposed vertically at predetermined intervals. The face image acquisition unit 304 monitors the output of each of the plurality of sensors and measures the body height of the user from the difference in the output value of each sensor (the output of each voltage value if infrared distance sensors are used). That is, if the body height of the user is low, fewer sensors react to the user. If the body height of the user is high, more sensors react to the user. The face image acquisition unit 304 determines the body height of the user based on the outputs of the sensors that change depending on the body height of the user. That is, the face image acquisition unit 304 determines the body height of the user based on the locations of the sensors that react to the body height of the user.

Alternatively, before acquiring a face image for authentication (matching), the face image acquisition unit 304 may determine the body height of the user by capturing an image of the user and analyzing the obtained image. In this case, the luminance of the upper light 404 and the luminance of the lower light 405 are set to initial values (default values).

When the face image acquisition unit 304 acquires a body height determination image, the face image acquisition unit 304 extracts a face area from the image. The face image acquisition unit 304 determines (estimates) the body height of the user based on the location of the extracted face image in the above body height determination image. Specifically, if the face image is located at an upper portion in the original image, the face image acquisition unit 304 estimates that the body height of the user is high. In contrast, if the face image is located at a lower portion in the original image, the face image acquisition unit 304 estimates that the body height of the user is low.

Alternatively, a learning model obtained by machine learning may be used to determine the body height of the user. For example, a learning model is generated by preparing many teaching data including images of users and body heights of the users as labels. The face image acquisition unit 304 may acquire a body height by entering a body height determination image to the generated learning model. Any algorithm, such as support vector machine, boosting, or neural network, may be used to generate the learning model. Since known techniques can be used for the above algorithms such as support vector machine, description thereof will be omitted.

As described above, without determining the body height of the user, the gate apparatus 10 may control the luminance of the upper light 404 and the luminance of the lower light 405 based on the face detection by image processing or the output values of sensors.

The passport possession determination unit 305 is means for determining whether the user possesses a correct passport. The passport possession determination unit 305 acquires MRZ information written in a Machine Readable Zone in a passport by controlling the scanner 402. The passport possession determination unit 305 reads out information stored in an IC chip by using the acquired MRZ information.

As described in "Measures for Safety of IC Passports" in the following reference document 1, information stored in an IC chip in a passport is encrypted (converted) by using MRZ information written in the same passport as a password.

Reference Document 1 https://www.mofa.go.jp/mofaj/toko/passport/ic_faq.html#11

The passport possession determination unit 305 decrypts information read out from an IC chip by using MRZ information acquired by the scanner 402 and acquires a face image stored in the IC chip.

The passport possession determination unit 305 extracts feature points from the face image acquired from the face image acquisition unit 304 and the face image acquired from the IC chip. Since an existing technique can be used to extract these feature points, detailed description of the extraction will be omitted. For example, the passport possession determination unit 305 extracts the eyes, nose, mouth, etc. as feature points from the individual face image. Next, the passport possession determination unit 305 calculates, as feature values, the location of the individual feature point and the distance between feature points and generates a feature vector formed by a plurality of feature values (vector information that features the face image).

The passport possession determination unit 305 calculates the similarity between two sets of feature values (feature vectors). For this similarity, the chi-squared distance, the Euclidean distance, or the like may be used. A longer distance represents a lower similarity, and a shorter distance represents a higher similarity.

If the above calculated similarity is more than or equal to a predetermined value, the passport possession determination unit 305 determines that the matching has succeeded. That is, if the above calculated similarity is more than or equal to a predetermined value, the passport possession determination unit 305 determines that each of the two face images is an image obtained by capturing the face of the same person.

If the 1-to-1 matching succeeds, the passport possession determination unit 305 determines that the user standing in front of the corresponding gate apparatus 10 possesses a correct passport. The passport possession determination unit 305 notifies the left-behind baggage alert unit 307 and the gate control unit 308 of the determination result (whether or not the user possesses a correct passport).

The baggage detection unit 306 is means for detecting whether there is an object in the baggage placement area 430. The baggage detection unit 306 monitors the output of the object detector 409. If the detector (an object detection sensor) detects presence of an object, the baggage detection unit 306 sets the "baggage detection flag" to "1". In addition, if the baggage detection unit 306 no longer detects presence of the object from the output of the object detector 409, the baggage detection unit 306 clears the "baggage detection flag" to "0".

The left-behind baggage alert unit 307 is means for giving, if there is an object in the baggage placement area 430, an alert about the left-behind baggage. More specifically, if the left-behind baggage alert unit 307 determines that the user has forgotten to take his or her baggage away from the baggage placement area 430, the left-behind baggage alert unit 307 outputs an alert about the left-behind baggage. The left-behind baggage alert unit 307 checks the baggage detection flag, upon completion of the emigration and immigration examination by the corresponding gate apparatus 10.

More specifically, the left-behind baggage alert unit 307 determines the situation in which the corresponding gate apparatus 10 has received an examination result from the server apparatus 20 via the communication control unit 301 and has received a determination result from the passport possession determination unit 305 as "completion of the emigration and immigration examination". The left-behind baggage alert unit 307 checks the baggage detection flag when the corresponding gate apparatus 10 has received the two results (the examination result and the determination result).

If the baggage detection flag indicates "1" at the above timing, the left-behind baggage alert unit 307 determines that the user has forgotten to take away his or her baggage and outputs an alert about the baggage. For example, the left-behind baggage alert unit 307 displays information as illustrated in FIG. 12 on the display 401. Alternatively, the left-behind baggage alert unit 307 may output an audio message notifying that the user has left behind his or her baggage from a speaker. Alternatively, the left-behind baggage alert unit 307 may notify a terminal held by the user that the user has left behind his or her baggage.

The gate control unit 308 is means for controlling the gate 408 of the gate apparatus 10. If there is no object at least in the baggage placement area 430, the gate control unit 308 controls the gate 408 such that the examination target user can pass through the gate 408. In other words, if there is an object (baggage) in the baggage placement area 430, the gate control unit 308 controls the gate 408 such that the examination target user cannot pass through the gate 408.

Specifically, when three conditions are met, the gate control unit 308 opens the gate 408. More specifically, when the examination result from the server apparatus 20 indicates "emigration and immigration permitted", the passport possession determination result indicates "possession of passport", and the baggage detection flag indicates "0", the gate control unit 308 opens the gate 408. In principle, unless the above three conditions are met, the gate control unit 308 does not open the gate 408.

The gate control unit 308 closes the gate 408 after the user who is allowed to pass through the gate 408 (the user who has passed the emigration and immigration examination) passes through the gate 408.

The storage unit 309 is means for storing information necessary for the operation of the gate apparatus 10.

[Operation of Emigration and Immigration Examination System]

Next, an operation of the emigration and immigration examination system according to the first example embodiment will be described.

Figure 13:
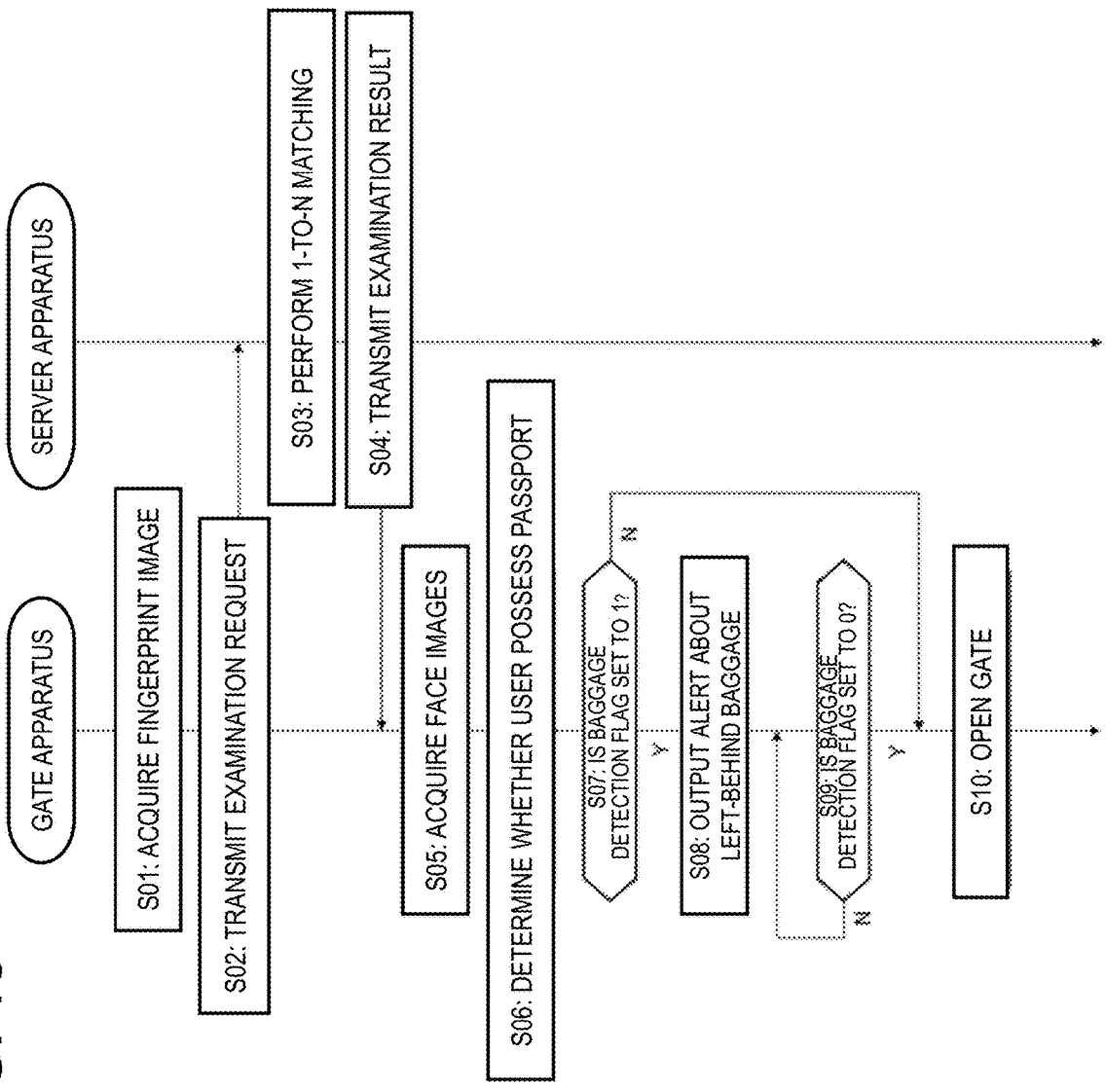
FIG. 13 is a sequence diagram illustrating an example of an operation of the emigration and immigration examination system according to the first example embodiment.

FIG. 13 is a sequence diagram illustrating an example of an operation of the emigration and immigration examination system according to the first example embodiment. FIG. 13 is a sequence diagram illustrating an example of a system operation performed on the departure date of a user. The following example assumes that the user has previously registered his or her "gate user information (fingerprint image)" in the server apparatus 20 before the operation in FIG. 13.

The user who has performed the pre-registration for use of the system moves to a gate apparatus 10 and stands in front of the gate apparatus 10. The gate apparatus 10 acquires a fingerprint image of the user (step S01).

The gate apparatus 10 transmits an examination request including the fingerprint image to the server apparatus 20 (step S02).

The server apparatus 20 performs 1-to-N matching by setting the acquired fingerprint image as the matching target fingerprint image (authentication target fingerprint image) and the fingerprint images stored in the registered user database as the registered fingerprint images (step S03).

The server apparatus 20 transmits an examination result (emigration and immigration permitted or emigration and immigration not permitted) obtained as a result of the 1-to-N matching to the gate apparatus 10 that has transmitted the examination request (step S04).

As described above, the gate apparatus 10 acquires a fingerprint image of the examination target user. Next, by transmitting an examination request including the acquired fingerprint image to the server apparatus storing the fingerprint images of the users whose emigration and immigration is permitted, the gate apparatus 10 requests the server apparatus to perform the emigration and immigration examination on the examination target user. The server apparatus 20 determines an examination result by performing matching (1-to-N matching) using the previously registered fingerprint images and transmits the examination result to the gate apparatus 10.

The gate apparatus 10 captures an image of the user to acquire a face image and reads out a face image from an IC chip in the passport (acquire face images; step S05). When capturing an image of the user, the gate apparatus 10 estimates the body height of the user and controls the two light sources such that the luminance suitable for the body height of the user can be obtained.

The gate apparatus 10 performs 1-to-1 matching using the two face images and determines whether the user possess a correct passport (step S06). The gate apparatus 10 acquires a first face image of the examination target user by controlling the camera device 403. Next, the gate apparatus 10 acquires a second face image stored in the passport possessed by the examination target user. By performing matching between the first and second face images, the gate apparatus 10 determines whether the examination target user possesses a correct passport.

In parallel to the above steps S01 to S06, the gate apparatus 10 detects whether baggage is placed in the baggage placement area 430. Specifically, the gate apparatus 10 monitors the output of the object detector 409, to detect the state of the baggage placement area 430. If there is baggage placed in the baggage placement area 430, the baggage detection flag is set to "1". If the baggage has been removed from the baggage placement area 430, the baggage detection flag is cleared to "0".

When the gate apparatus 10 completes the emigration and immigration examination (when the gate apparatus 10 receives an examination result from the server apparatus 20 and completes the passport possession determination), the gate apparatus 10 checks whether the baggage detection flag is set to "1" (step S07).

If the baggage detection flag is set to "1" (Yes in step S07), the gate apparatus 10 outputs an alert about the left-behind baggage (step S08).

As described above, when the gate apparatus 10 receives an examination result from the server apparatus 20 and completes the passport possession determination, if there is an object in the baggage placement area 430, the gate apparatus 10 outputs an alert about the left-behind baggage.

If there is an object in the baggage placement area 430, the gate apparatus 10 sets the baggage detection flag. If there is no object in the baggage placement area 430, the gate apparatus 10 clears the baggage detection flag. The gate apparatus 10 determines whether there is left-behind baggage by performing the above control processing of the baggage detection flag and by checking the baggage detection flag when the gate apparatus 10 receives an examination result from the server apparatus 20 and completes the passport possession determination.

The gate apparatus 10 continuously monitors the baggage placement area 430 to detect whether the baggage has been taken away from the baggage placement area 430. That is, the gate apparatus 10 continuously monitors the baggage detection flag (step S09).

If the baggage detection flag is cleared to "0" (Yes in step S09), the examination result from the server apparatus 20 indicates "emigration and immigration permitted", and the user possesses a "correct passport", the gate apparatus 10 opens the gate 408 (step S10). Thus, if the examination result from the server apparatus 20 indicates emigration and immigration permitted, the examination target user possesses a correct passport, and there is no object in the baggage placement area 430, the gate apparatus 10 controls the gate 408 such that the examination target user can pass through the gate 408. In other words, if the examination result from the server apparatus 20 indicates "emigration and immigration not permitted" or the examination target user does not possess a correct passport, the gate apparatus 10 controls the gate 408 such that the examination target user cannot pass through the gate 408.

As described above, the gate apparatus 10 according to the first example embodiment transmits a matching request (an examination request) using biological information (a fingerprint image) to the server apparatus 20 and receives a matching result (an examination result) from the server apparatus 20. In addition, the gate apparatus 10 controls the two light sources such that the face of the user is illuminated with light with uniform illuminance and acquires a face image. The gate apparatus 10 performs matching between this acquired face image and the face image read out from an IC chip in the passport, to determine whether the user possesses a correct passport. If the gate apparatus 10 determines that the examination target user has forgotten to take away his or her baggage from the baggage placement area 430, the gate apparatus 10 alerts the user about the left-behind baggage. Unless the user takes away the baggage from the baggage placement area 430, the gate apparatus 10 does not open the gate 408 even if the emigration and immigration examination on the user has been completed. As a result, the gate apparatus 10 can prevent the user from leaving the baggage placement area 430 without his or her baggage.

In addition, by controlling the two light sources (the upper light 404 and the lower light 405) based on the body height of the user, the gate apparatus 10 according to the first example embodiment can obtain a face image suitable for face matching. That is, by optimally controlling the luminances of the different lights, the gate apparatus 10 can obtain a high quality image (a face image), regardless of the body height of the user. More specifically, the gate apparatus 10 changes the luminance of the light emitted from the upper light 404 and the luminance of the light emitted from the lower light 405 such that the user is illuminated with uniform illuminance. As a result, for example, the brightness of the light emitted to the face or the like does not vary depending on the location, and biological information suitable for authentication is acquired.

In addition, in the case of the gate apparatus 10 according to the first example embodiment, the upper light 404 is attached to the ceiling portion 407. This light with a roof (the upper light 404 embedded into the ceiling portion 407) blocks the outside light, etc. As a result, the gate apparatus 10 can create an environment suitable for acquiring a face image of a user, regardless of the time of the day or the like. That is, since the gate apparatus 10 includes a light with a roof, the accuracy of the face authentication can be prevented from being deteriorated by disturbance. In addition, the light with a roof is hung by the supporting portion 406, and the supporting portion 406 is shaped in a thick flat plate. In this way, the display 401 can be installed and wiring can be made inside the supporting portion 406.

[Variation]

The configurations, operations, etc. of the emigration and immigration examination systems according to the above example embodiments are examples and do not limit the system configuration, etc. For example, in the above example embodiments, when the gate apparatus 10 acquires biological information about a face image, the gate apparatus 10 controls the luminance of the upper light 404 and the luminance of the lower light 405. However, this control on the two light sources is also applicable to when an iris image is acquired for authentication or when a fingerprint image is acquired for authentication. That is, when an iris image or a fingerprint image is acquired, the two light sources may be controlled such that an eye area or a finger is illuminated with light with uniform luminance.

For example, the function of the server apparatus 20 may entirely or partly be realized by the gate apparatus 10. For example, the registered user database may be configured in the gate apparatus 10, and the gate apparatus 10 may perform the emigration and immigration examination on the examination target user by using this database. Alternatively, the registered user database of the server apparatus 20 may be configured in a different database server.

In the above example embodiments, after whether a fingerprint image acquired from a user is registered in the server apparatus 20 is determined, whether the user possesses a correct passport is determined. However, these two determinations may be performed in parallel or in the reverse order. That is, after whether a user possesses a correct passport is determined, whether a fingerprint image acquired from the user is registered in the server apparatus 20 may be determined.

In the above example embodiments, while a fingerprint image acquired by the gate apparatus 10 is used to determine a user who has previously completed the emigration and immigration examination, the fingerprint image may be used to determine whether the user is a criminal or the like. For example, the server apparatus 20 may perform matching between an acquired fingerprint image and the fingerprint images stored in a blacklist in which fingerprints of criminals are listed.

While the above example embodiments have been described based on a case in which fingerprint images are stored as biological information in the server apparatus 20, other biological information may be alternatively stored in the server apparatus 20. For example, face images, voice-print information, iris information, or the like or feature values thereof may be stored as biological information. Likewise, when biological information other than a face image can be acquired from a passport, the biological information other than a face image may be used to determine whether the examination target user possesses a correct passport.

The data exchange mode between the individual gate apparatus 10 and the server apparatus 20 is not limited to a particular mode. The data exchanged between these apparatuses may be encrypted. The fingerprint images are personal information, and to appropriately protect the personal information, it is desirable that encrypted data be exchanged. The gate apparatus 10 may transmit an examination request having a digital signature to the server apparatus 20. If the server apparatus 20 succeeds in verifying the digital signature, the server apparatus 20 may process the acquired examination request. Thus, the server apparatus 20 may be configured to verify the validity of the gate apparatus 10 as the examination request transmission source by verifying a digital signature.

While the above example embodiments have been described based on a case in which information is acquired by using MRZ information in an IC chip in a passport, the technique disclosed in the present application is also applicable to other cases. That is, when information is read out from an IC chip mounted on a card or the like similar to a passport, information corresponding to MRZ information may be used.

While the above example embodiments have been described based on a case in which each of the upper light 404 and the lower light 405 is formed by a single light source, any one of the upper light 404 and the lower light 405 may be formed by a plurality of light sources. In this case, by controlling the number of light sources to be lit among the plurality of light sources, the face image acquisition unit 304 may change the luminance of the upper light 404 or the lower light 405. That is, by performing digital control on the plurality of light sources, the gate apparatus 10 may control the luminance of the light emitted to the face of the user.

While the above example embodiments have been described based on a case in which two light sources (the upper light 404 and the lower light 405) are attached to the gate apparatus 10, a middle light may also be attached to the gate apparatus 10 in addition to the above two light sources. That is, a middle light may be installed between the upper light 404 and the lower light 405, and the luminance of the middle light may be controlled. In this case, the face image acquisition unit 304 may control the luminances of the three light sources based on the body height of the user. That is, the gate apparatus 10 controls the luminances of the plurality of light sources such that the user is illuminated with light with uniform illuminance.

While the above example embodiments have been described based on a case in which the luminance of the light emitted from each of a plurality of light sources is controlled based on the body height of the user, the above luminances may be controlled based on other information. For example, the luminances of the light sources may be controlled based on the length of the user's hair and whether the user is wearing glasses. Alternatively, the luminances of the light sources may be controlled by comprehensively taking a plurality of elements (the body height and the presence or absence of glasses) into account. Specifically, the luminances of the lights emitted from the two light sources may be different between a tall user with glasses and a short user with glasses. Whether the user is wearing glasses can be determined by performing image processing using a template or by using a learning model obtained by machine learning.

The gate apparatus 10 may analyze a captured face image and control the luminances of the two light sources based on the analysis result of the face image. For example, the gate apparatus 10 (the face image acquisition unit 304) divides a face image into a plurality of areas and calculates an average brightness value of pixels constituting each of the plurality of small areas. The gate apparatus 10 may control the two light sources such that the calculated average value indicates a predetermined value or more and the variation in brightness among the small areas (for example, the variance value or standard deviation) becomes smaller than a threshold. That is, the gate apparatus 10 may feed the analysis result of the captured face image back to the control of the two light sources, to acquire a face image having uniform brightness.

The gate apparatus 10 may determine the content of the alert about left-behind baggage by using information obtained from the passport. Specifically, the left-behind baggage alert unit 307 may change the content of the message or the display method based on information obtained from an MRZ or an IC chip in the passport. For example, the left-behind baggage alert unit 307 may generate an alert message by using the name of the user. For example, if the name of the user is "Taro", the left-behind baggage alert unit 307 may output an alert message "Mr. Taro, please take your baggage with you".

Alternatively, the left-behind baggage alert unit 307 may change the language of the alert message based on the nationality of the user. For example, if the nationality of the user is Japan, the left-behind baggage alert unit 307 may output an alert message in Japanese (display an alert message in Japanese on display 401 or output an audio message in Japanese from a speaker). If the nationality of the user is China, the left-behind baggage alert unit 307 may output an alert message in Chinese. Alternatively, the left-behind baggage alert unit 307 may generate a plurality of alert messages in a plurality of languages. For example, the left-behind baggage alert unit 307 may generate an alert message in "English" as its fixed first language and an alert message in a language corresponding to the nationality of the user as its second language.

When alerting the examination target user about left-behind baggage by an audio message, the left-behind baggage alert unit 307 may use a parametric speaker or the like having a strong directivity. By using a parametric speaker or the like, the left-behind baggage alert unit 307 can reliably send an alert message to the user.

In the flowcharts and sequence diagrams used in the above description, a plurality of steps (processes) are sequentially described. However, the order of the execution of the steps performed in the individual example embodiment is not limited to the described order. In the individual example embodiment, the order of the illustrated steps may be changed to the extent that a problem is not caused on the content of the individual example embodiment. For example, individual processes may be executed in parallel.

The above example embodiments have been described in detail to facilitate the understanding of the present application disclosed and not to mean that all the configurations described above are needed. In addition, if a plurality of example embodiments have been described, each of the example embodiments may be used individually or a plurality of example embodiments may be used in combination. For example, part of a configuration according to one example embodiment may be replaced by a configuration according to another example embodiment. For example, a configuration according to one example embodiment may be added to a configuration according to another example embodiment. In addition, addition, deletion, or replacement is possible between part of a configuration according to one example embodiment and another configuration.

The industrial applicability of the present invention has been made apparent by the above description. That is, the present invention is suitably applicable, for example, to emigration and immigration examination systems at airports.

A part or the entirety of the example embodiments described above may be described as in the following supplementary notes, but is not limited to the followings.

[Supplementary Note 1]
A Gate Apparatus Including:
an acquisition unit that acquires biological information about a user;
an upper light that emits light from above the user;
a lower light that emits light from below the user; and a light control unit that changes luminance of the light emitted from the upper light and luminance of the light emitted from the lower light when the biological information about the user is acquired.

[Supplementary Note 2]
The gate apparatus according to supplementary note 1, wherein the light control unit changes the luminance of the light emitted from the upper light and the luminance of the light emitted from the lower light such that the user is illuminated with light with uniform illuminance.

[Supplementary Note 3]
The gate apparatus according to supplementary note 1 or 2, wherein the light control unit changes the luminance of the light emitted from the upper light and the luminance of the light emitted from the lower light based on a physical feature of the user.

[Supplementary Note 4]
The gate apparatus according to supplementary note 3, wherein the light control unit changes the luminance of the light emitted from the upper light and the luminance of the light emitted from the lower light based on a body height of the user.

[Supplementary Note 5]
The gate apparatus according to supplementary note 4, wherein, when the body height of the user is higher than a first threshold, the light control unit sets the luminance of the lower light to be higher than the luminance of the upper light.

[Supplementary Note 6]
The gate apparatus according to supplementary note 5, wherein, when the body height of the user is lower than a second threshold, the light control unit sets the luminance of the upper light to be higher than the luminance of the lower light.

[Supplementary Note 7]
The gate apparatus according to any one of supplementary notes 4 to 6, wherein the light control unit extracts a face area from an image captured from the user and changes the luminance of the light emitted from the upper light and the luminance of the light emitted from the lower light based on a location of the extracted face area in the captured image.

[Supplementary Note 8]
The gate apparatus according to any one of supplementary notes 4 to 6, further including a plurality of sensors that are disposed vertically upward from a main body and that detect the body height of the user, wherein the light control unit changes the luminance of the light emitted from the upper light and the luminance of the light emitted from the lower light based on an output value obtained from each of the plurality of sensors.

[Supplementary Note 9]
The gate apparatus according to any one of supplementary notes 1 to 8, wherein the light control unit controls the luminance of the light emitted from the upper light and the luminance of the light emitted from the lower light, to acquire an image suitable for face authentication.

[Supplementary Note 10]
A control method of a gate apparatus including an upper light that emits light from above a user and a lower light that emits light from below the user, the control method comprising:
changing luminance of the light emitted from the upper light and luminance of the light emitted from the lower light; and
acquiring biological information about the user.

[Supplementary Note 11]
A computer-readable storage medium storing a program that causes a computer mounted on a gate apparatus including an upper light that emits light from above a user and a lower light that emits light from below the user to perform processing for:
changing luminance of the light emitted from the upper light and luminance of the light emitted from the lower light; and
acquiring biological information about the user.

The supplementary notes 10 and 11 can be expanded in the same way as the supplementary note 1 can be expanded into the supplementary note 2 to the supplementary note 9.

The entire disclosure of the above patent literature is incorporated herein by reference thereto. While the example embodiments of the present invention have thus been described, the present invention is not limited to these example embodiments. It is to be understood to those skilled in the art that these example embodiments are only examples and that various variations are possible without departing from the scope and sprit of the present invention. That is, the present invention of course includes various variations and modifications that could be made by those skilled in the art in accordance with the overall disclosure including the claims and the technical concept.

REFERENCE SIGNS LIST 10, 10-1 to 10-3, 100 gate apparatus
20 server apparatus
101, 404 upper light
102, 405 lower light
103 light control unit
104 acquisition unit
201, 301 communication control unit
202 fingerprint image registration unit
203 examination unit
204, 309 storage unit
211, 311 processor
212, 312 memory
213 input-output interface
214, 313 communication interface
302 fingerprint image acquisition unit
303 examination request unit
304 face image acquisition unit
305 passport possession determination unit
306 baggage detection unit
307 left-behind baggage alert unit
308 gate control unit
401 display
402 scanner
403 camera device 406 supporting portion
407 ceiling portion
408 gate
409 object detector
430 baggage placement area
431 top board area
432 side area

What is claimed is:

1. A gate apparatus comprising:
an upper light that emits light from above a user;
a lower light that emits light from below the user;
at least one memory storing a set of instructions; and
at least one processor configured to execute the set of instructions to:
acquire biological information about a user; and
change luminance of the light emitted from the upper light and luminance of the light emitted from the lower light based on a physical feature of the user that is a body height of the user, when the biological information about the user is acquired,
wherein, when the body height of the user is higher than a first threshold, the at least one processor sets the luminance of the lower light to be higher than the luminance of the upper light.

2. The gate apparatus according to claim 1, wherein
the at least one processor changes the luminance of the light emitted from the upper light and the luminance of the light emitted from the lower light such that the user is illuminated with light with uniform illuminance.

3. The gate apparatus according to claim 1, wherein when the body height of the user is lower than a second threshold, the at least one processor sets the luminance of the upper light to be higher than the luminance of the lower light.

4. The gate apparatus according to claim 1, wherein
the at least one processor is further configured to execute the set of instructions to:
extract a face area from an image captured from the user and change the luminance of the light emitted from the upper light and the luminance of the light emitted from the lower light based on a location of the extracted face area in the captured image.

5. The gate apparatus according to claim 1, further comprising a plurality of sensors that are disposed vertically upward from a main body and that detect the body height of the user, wherein
the at least one processor changes the luminance of the light emitted from the upper light and the luminance of the light emitted from the lower light based on an output value obtained from each of the plurality of sensors.

6. The gate apparatus according to claim 1, wherein
the at least one processor is further configured to execute the set of instructions to:
control the luminance of the light emitted from the upper light and the luminance of the light emitted from the lower light, to acquire an image suitable for face authentication.

7. A control method of a gate apparatus including an upper light that emits light from above a user and a lower light that emits light from below the user, the control method comprising:
acquiring biological information about a user; and
changing luminance of the light emitted from the upper light and luminance of the light emitted from the lower light based on a physical feature of the user that is a body height of the user, when the biological information about the user is acquired,
wherein, when the body height of the user is higher than a first threshold, the control method sets the luminance of the lower light to be higher than the luminance of the upper light.

8. A non-transitory computer-readable storage medium storing a program that causes a computer mounted on a gate apparatus including an upper light that emits light from above a user and a lower light that emits light from below the user to perform processing comprising:
acquiring biological information about a user; and
changing luminance of the light emitted from the upper light and luminance of the light emitted from the lower light based on a physical feature of the user that is a body height of the user, when the biological information about the user is acquired,
wherein, when the body height of the user is higher than a first threshold, the control method sets the luminance of the lower light to be higher than the luminance of the upper light.

* * * * *